United States Patent
Gazenko (12)

(10) Patent No.: US 7,781,159 B2
(45) Date of Patent: *Aug. 24, 2010

(54) MICROMETHOD AND DEVICE FOR RAPID DETECTION, ENUMERATION AND IDENTIFICATION OF ENTITIES

(75) Inventor: Sergey Gazenko, Mason, OH (US)

(73) Assignee: Nanologix, Inc., Hubbard, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/141,677

(22) Filed: May 9, 2002

(65) Prior Publication Data

US 2003/0211566 A1 Nov. 13, 2003

(51) Int. Cl.
- *C12Q 1/00* (2006.01)
- *C12Q 1/02* (2006.01)
- *G01N 33/53* (2006.01)
- *G01N 33/554* (2006.01)
- *C12N 11/00* (2006.01)

(52) U.S. Cl. .................. 435/4; 435/7.1; 435/7.2; 435/7.32; 435/29; 435/174

(58) Field of Classification Search ............. 435/34, 435/284, 287, 288.4, 288.5, 288.7, 296, 301, 435/4, 7, 2, 7.32
See application file for complete search history.

(56) References Cited

U.S. PATENT DOCUMENTS

| | | | |
|---|---|---|---|
| 5,624,815 A | 4/1997 | Grant et al. | |
| 5,650,323 A | 7/1997 | Root | |
| 5,660,990 A | 8/1997 | Rao et al. | |
| 5,716,798 A * | 2/1998 | Monthony et al. | 435/34 |
| 5,770,440 A | 6/1998 | Berndt | |
| 6,043,027 A | 3/2000 | Selick et al. | |
| 6,372,183 B1 | 4/2002 | Akong et al. | |
| 6,377,721 B1 | 4/2002 | Walt et al. | |
| 6,696,286 B1 | 2/2004 | Halverson et al. | |
| 6,716,629 B2 | 4/2004 | Hess et al. | |
| 6,729,352 B2 | 5/2004 | O'Connor et al. | |
| 6,743,581 B1 * | 6/2004 | Vo-Dinh | 435/6 |
| 6,767,706 B2 * | 7/2004 | Quake et al. | 435/6 |
| 6,818,435 B2 * | 11/2004 | Carvalho et al. | 435/286.5 |
| 6,852,222 B2 | 2/2005 | Lautenschlager et al. | |
| 7,125,674 B2 | 10/2006 | Beattie | |
| 7,338,773 B2 | 3/2008 | Goldbard et al. | |
| 2002/0153046 A1 | 10/2002 | Dantsker et al. | |
| 2002/0189374 A1 | 12/2002 | DeSilets et al. | |
| 2003/0096268 A1 | 5/2003 | Weiner et al. | |
| 2006/0088895 A1 | 4/2006 | Wanders et al. | |

OTHER PUBLICATIONS

Yang et al. "Cell Docking and On-Chip Monitoring of Cellular Reactions with a Controlled Concentration Gradient on a Microfluidic Device"; Analytical Chemistry, vol. 74, No. 16 (2002) pp. 3991-4001.*
Moorthy et al. "In Situ fabricated porous filters for Microsystems"; Lab-on-a Chip, vol. 3 (2003) pp. 62-66.*
Thiébaud et al. "PDMS device for patterned application of microfluids to Neuronal cells arranged by microcontact printing"; Biosensors and Bioelectronics, vol. 17 (2002) pp. 87-93.*
Walker et al. "Insect Cell Culture in Microfluidic Channels"; Biomedical Microdevices, vol. 4, No. 3 (2002) pp. 161-166.*
Martin et al. "Generation of larger numbers of separated microbial populations by cultivation in segmented-flow microdevices"; Lab-on-a-Chip, vol. 3 (2003) pp. 202-207.*
Martin, Paul, Office Action for U.S. Appl. No. 11/393,012, entitled "Method and device for rapid detection of microorganisms by changing the shape of micro-colonies," mailed Feb. 19, 2008 (1).
Diramio, Jacqueline A., Office Action for U.S. Appl. No. 11/109,857, entitled "Device for rapid detection and identification of single microorganisms without preliminary growth," mailed Sep. 24, 2008 (4).
Diramio, Jacqueline A, Office Action for U.S. Appl. No. 11/109,857, entitled "Device for rapid detection and identification of single microorganisms without preliminary growth," mailed May 21, 2008 (3).
Diramio, Jacqueline A, Advisory Action for U.S. Appl. No. 11/109,857, entitled "Device for rapid detection and identification of single microorganisms without preliminary growth," mailed Feb. 5, 2008 (2a).
Diramio, Jacqueline A, Office Action for U.S. Appl. No. 11/109,857, entitled "Device for rapid detection and identification of single microorganisms without preliminary growth," mailed Nov. 13, 2007 (2).

(Continued)

*Primary Examiner*—Vanessa L. Ford
(74) *Attorney, Agent, or Firm*—Thompson Hine LLP

(57) ABSTRACT

This invention describes a method and device for the rapid detection, enumeration and identification of microorganisms. It is based on the production and accumulation of absorbent or fluorescent molecules during reactions between artificial substrates and enzymes in micro-channels of the sampling-detecting unit, which is a part of a sample treating device. The enzymes of cells, or enzymes attached to the cell body through antibody-enzyme conjugates, produce easily detectable concentration of colored or fluorescent molecules in a small volume much faster than in a large volume. Channels that contain microorganisms appear as colored or fluorescent dots when viewed using a light or fluorescent microscope.

11 Claims, 2 Drawing Sheets

OTHER PUBLICATIONS

Diramio, Jacqueline A, Office Action for U.S. Appl. No. 11/109,857, entitled "Device for rapid detection and identification of single microorganisms without preliminary growth," mailed May 29, 2007 (1).

Harle, Jennifer, Office Action for U.S. Appl. No. 10/628,110, entitled "Method for rapid detection of microorganisms by changing the shape of micro colonies," mailed Oct. 27, 2005 (2).

Harle, Jennifer, Office Action for U.S. Appl. No. 10/628,110, entitled "Method for rapid detection of microorganisms by changing the shape of micro colonies," mailed Nov. 9, 2004 (1).

International Preliminary Report on Patentability, International Application No. PCT/US2006/015321, entitled "Device For Rapid Detection and Identification Of Single Microorganisms Without Preliminary Growth," mailed Nov. 1, 2007.

International Search Report, International Application No. PCT/US2006/015321, entitled "Device For Rapid Detection And Identification Of Single Microorganisms Without Preliminary Growth," published Oct. 26, 2006.

BioTK—Projects partnering—Project details, To Change the face of modem microbiological diagnostics, PHARM techexpo, www.biotk.com/partnering_details.php?id=15, Jul. 24, 2004, printed Nov. 25, 2008.

* cited by examiner

MICROMETHOD AND DEVICE FOR RAPID DETECTION, ENUMERATION AND IDENTIFICATION OF ENTITIES

BACKGROUND OF THE INVENTION

Modern methods for the detection, enumeration and identification of microorganisms fall into two main categories. The first provides analysis after preliminary growth on a special nutrient media. The second category doesn't require preliminary growth. Methods utilized in the first category utilizes several different chemical, biochemical, physical, optical techniques, and requires many hours or days for preliminary growth in order to produce enough homogeneous cells or colonies for detection. The second category utilizes methods of Microscopy, Flow Cytometry or polymerase chain reaction (PCR). These methods allow for analysis immediately after sampling and sample treatment. Analyzing a single cell without preliminary growth belongs to these rapid micro-methods.

Microscopy (light and fluorescent, visual or automated) and Flow Cytometry (absorbent, fluorescent or scattering) needs a treatment of cell body by an absorbent or fluorescent dyes. Utilization of antibodies with attached fluorescent molecules helps in rapid identification of single cells. A higher concentration of colored molecules increases the reliability of analysis.

One of the well known markers for detection and identification of cells are artificial substrates—non colored or fluorescent substances cleaved by enzymes or enzymatic groups with the production of light-absorbent or fluorescent molecules. Artificial substrates are broadly used for the detection of live microorganisms, detection by unique enzyme, identification by enzymatic profiles, or utilizing in Enzyme-Immunogical Analysis (EIA). Some of the artificial substrates produce non-soluble intracellular precipitates (e.g. Tetrazolium salts, Fluorescein based substrates in acidic environments, Rezorufin and others). This feature is useful for Microscopy and Flow Cytometry because of the production of specifically colored cell bodies. Other substrates produce soluble derivatives that are excreted from the cells and color the buffer solution (e.g. 4-Methylumbelliferone, Tetramethylbenzidine, Fluorescein in alkaline environments and others). This group of artificial substrates could produce a large amount of absorbent or fluorescent molecules because they don't accumulated in cells and don't oppress biochemical pathways of living cells as precipitates' do.

Retention of fluorescent or absorbent molecules excreted from cells or produced in EIA in a small space around a single cell could create easily detectable concentration of these molecules. Utilization of this useful feature of soluble absorbent or fluorescent molecules together with inventing a simple hand-held device for cell sampling and their immediately treating for detection or identification purposes is the subject of the present invention.

Simple and rapid detection, enumeration and identification of single prokaryotic or eukaryotic cells is very important for medical microbiology, cytology, environmental science, finding of pollutants microorganisms in food and pharmaceutical industry, epidemiology, public and military defense, scientific research and other areas.

SUMMARY OF INVENTION

Referring to FIGS. 1 and 2, the present invention is based on the production and accumulation of absorbent or fluorescent molecules during reactions between artificial substrates (AS) and enzymes in the micro-channels 1 of the sampling-detecting unit (SDU) 2. The SDU contains a multitude of micro-channels 1 a membrane filter (filter layer) 3 for the retention of single particles or cells a solid base (rigid layer) 5, and an intermediate layer 4. Sampling realized by filtration from air or liquid. The SDU is part of a hand-held sampling device of FIG. 3 that looks like a cylinder with a forcer. It allows the trapping of cells in micro-channels, while allowing reagents and washing fluids to pass only in one direction: from the upper side to the lower side. The cells, if any in a sample, pass the micro-channels during sampling and are trapped on the filter surface. After this, a solution containing AS is added to the micro-channels 1. The AS reacts with the enzymes of live cells (detection of live cells) or with special indicator enzymes or with enzymes previously attached to cells through an antibody in an earlier wash (EIA version for single cell-single cell identification). After a short incubation period, from a few minutes to around an hour, a micro-channel containing a cell appears as a bright fluorescent or colored dot when viewed under a microscope. Therefore, a detectable concentration of fluorescent or colored molecules is reached only as a result of the accumulation of substrates in a very small volume, which is greater than the volume of a single cell by only several thousands times. FIG. 2 shows enlarged micro-channels 1 disposed on filter 3 for trapping of the cells, where one micro-channel 1 contains cell and colored molecules 6. An optical object that is greater than a cell by a thousand to tens thousand times could be easily detected with modem light or fluorescent optics. The positive effect of the accumulation of the products of colored reactions in very small volume is illustrated by the following calculations:

Lets divide one milliliter ($10^{12}$ $\mu m^3$) of liquid containing $25 \cdot 10^{\wedge}6$ cells on smaller parts. Each 0.2 ml ($10^{12}$ $\mu m^3$) (the well of 96-well plate) will contain $5 \cdot 10^{\wedge}6$ cells. One hundred cells will be in a volume $4 \cdot 10^{\wedge}6$ $\mu m^3$). Volume $4 \cdot 10^{\wedge}6$ $\mu m^3$ will contain only one cell. This volume corresponds to channel of SDU with dimensions: diameter of channel=10 $\mu m$ and length of channel=500 $\mu m$. All these volumes with cells, including the smallest, corresponding to the concentration $25 \cdot 10^{\wedge}6$ cells/ml. This high concentration of cells can produce easily detectable concentration of colored or fluorescent molecules from enzyme-artificial substrate reactions.

It means that one cell in $4 \cdot 10^{\wedge}4$ $\mu m^3$ (one channel of SDU) will produce the same easily detectable concentration of the same molecules in the same time as $25 \cdot 10^{\wedge}6$ cells in one ml or $5 \cdot 10^6$ cells in 0.2 ml.

This invention differs from other rapid micro-methods by utilizing the sampling-detection unit, which consists of an array of long, parallel, similar by size and shape, open-ended micro-channels for retaining the products of enzyme-substrate reactions from one single trapped cell. The processes of sampling and sample treatment occur in the same device. The results are detection, identification and enumeration of single entities within the SDU. These results could easily be found with usage of regular fluorescent or light microscope or other simple optical devices or automated instruments for microanalysis.

BRIEF DESCRIPTION OF THE DRAWINGS

The drawings included herewith are incorporated in and form a part of this specification. The drawings illustrate one embodiment of the present disclosure and, together with the description, serve to explain the principles of the invention. It should be understood that drawings referred to in this description are not drawn to scale unless specifically noted.

DETAILED DESCRIPTION OF THE INVENTION

Figure 1:
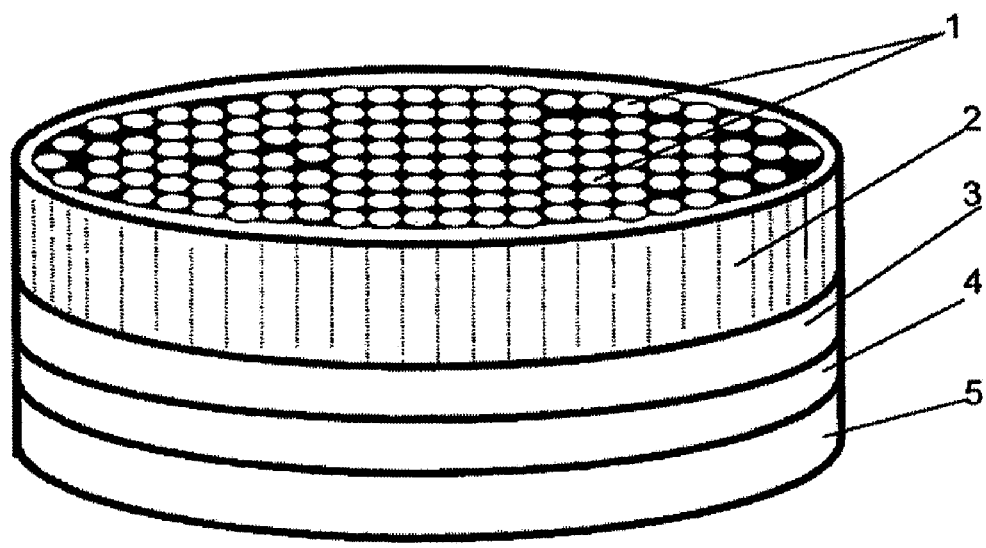
FIG. 1 is an isometric view of a sampling-detecting unit (SDU) having multiple microchannels in a FIG. 2 is an enlarged cross-sectional view of a several exemplary micro-channels, including one micro-channel with a trapped

This invention provides a simple device and method for sampling of cells from liquid or air, easy treatment procedures of single trapped cells and retention of colored molecules—products of reactions in very small volumes to reach detectable concentration.

It is well understood, and currently used in practice, that dividing a sample into small volumes helps to detect cell concentration faster. This effect depends on reaching a detectable concentration in a small volume faster rather than in a large volume. Thus, U.S. Pat. No. 5,716,798 describes the method for rapid detection of microorganisms in a container divided on a plurality of discrete zones, each of which can be separately monitored for microbial presence by reaching detectable cell concentrations after preliminary growth in some zones. This method gives timesaving of 10 to 40% in comparison with other methods. U.S. Pat. No. 5,770,440 is based on the same effect. The present invention differs from these patents by the analysis of a single cell. No time-consuming preliminary growth or nutrient media are necessary.

U.S. Pat. No. 4,959,301 is based on dividing a sample with viable biological entities in several micro-droplets and detecting entities by growth or by biochemical reactions of a single entity within a droplet. This method can indicate a single cell in less than 30 minutes in some variants. Nevertheless, it is technologically complicated. Micro-droplets are produced with different volumes and require statistical analysis for calculating results. This method could be reproduced only in a laboratory by highly professional personnel. The present invention has the following advantages:

The micro-channels have equal volume: no statistical analysis is necessary;

Droplets require special manipulations against drying, but micro-channels have a diameter/length=1/30-1/50 and, therefore, an extremely small square of evaporation. No special actions against drying are necessary;

The volume of a micro-channel is smaller than an average droplet, therefore detectable concentrations of AS could be reached faster.

The increasing of the detectable concentration in small volume used in ETA and ELISA, also. Thus, well-known 96-wells immunological plates are now produced with 384 and even 912 wells on the plate of the same size (128 mm×86 mm). A smaller volume gives the opportunity to reach a detectable concentration of absorbent or fluorescent molecules faster, or use smaller concentrations of homogeneous cells. Nevertheless, these plates and procedures of identification could be used only for identification of homogeneous cells in concentrations of hundreds-thousands cells per ml.

Our own experiments and calculations were done with vegetative cells *Bacillus cereus*. They show that one live cell of *Bacillus cereus* (TSA, 17 hours at 37° C.) produces around 3,000,000 fluorescent molecules of 4-Methylumbelliferone (MU) from 4-Methylumbelliferyl acetate (MUA) per minute. To find fluorescence by the naked eye in the quartz cell of fluorometer Perkin-Elmer LS-5 with maximum excitation 350 nm. needs a concentration of MU around $6 \cdot 10^{15}$ molecules per ml. This concentration in a volume $0.01$ mm$^3$ could be produced by one cell of *Bacillus cereus* in 2 minutes. To reach the same concentration in $0.1$ mm$^3$ needs 33 hours of one cell incubation. In 1 mm$^3$ needs 3.8 years of incubation. $0.02$ cm$^3$—76 years. $0.2$ cm$^3$ (the volume of 96-wells plate)—760 years. 1 cm$^3$—3800 years of incubation.

Thus, the volumes for reactions needs to be as small as possible to reach a detectable concentration in an acceptable time frame, but large enough to be detected by simple optical methods. Modern rapid micro-methods based on the concentration of dye in a cell body (Flow Cytometry, automated microscopy) requires special complicated techniques (scanning of surface, special flow stream device) to find a single cell on a filter, slide, or in a flow stream because of very small size of an object, around 0.5-5 μm$^3$.

The size of the object (fluorescent or colored micro-channel) according the present invention is thousands to tens thousands times larger. Therefore, simple optics with small multiplication could be employed. No special complicated technique is required to visualize the results. Thus, the present invention could be employed in field studies and does not require high level professionals. The price of analysis could be significantly reduced.

Another important part of this invention is the usage of artificial substrates for different enzymes or enzymatic groups for the production of detectable concentrations of absorbent or fluorescent molecules. Artificial substrates are broadly used for detection of enzymatic activities. Many different artificial substrates are based on chromogenic molecules such as 2-Nitrophenol, 4-Nitrophenol, 5-Bromo-4-chloro-3-indoxol, 3-Indoxol, 5-Bromo-6-chloro3-indoxol, 6-Chloro-3-indoxol, 5-Iodo-3-indoxol, N-Methylindoxol, 3,3',5,5'-Tetramethylbenzidine dihydrochloride and others. Other artificial substrates are based on fluorescent molecules such as 4-Methylumbelliferone, 7-Amido-4-methylcoumarin, Fluorescein, Eosine and others. They cover a large spectrum of different enzymes such as Glycosidases, Esterases, Phosphatases, Peptidases, Sulfatases, Dehydrogenases and special enzymes like Horseradish-Peroxidase, β-D-galactosidase or a specific aminopeptidase.

Different analytical methods could be produced using the device described in the present invention. Detection of a single live microorganism in a sample could be done with the use of artificial substrates for large groups of enzymes that are always present in any live microorganism. For example 4-Methylumbelliferyl phosphate for phosphatases, 4-Methylumbellyferyl acetate for esterases, or a mixture of both. Detection of some important microorganisms could also be done following exploration of their unique enzymes. For example, 4-Methylumbelliferyl-β-D-galactopyranoside is a reliable indicator of β-D-galactosidase, a unique enzyme of *Escherichia coli*.

Identification of a single cell trapped in a micro-channel could be done with an enzyme attached to an antibody, which attaches to antigens of an investigated cell: EIA version for a single cell.

Identification of a single cell could also be done by enzymatic profiles. In this case a trapped cell will produce a fluorescent product from the first substrate, which will be measured in amount of fluorescence and then washed out. After that, a second substrate will be applied and measured, followed by a third and so on. No special instrument for this purpose currently exists.

Figure 2:
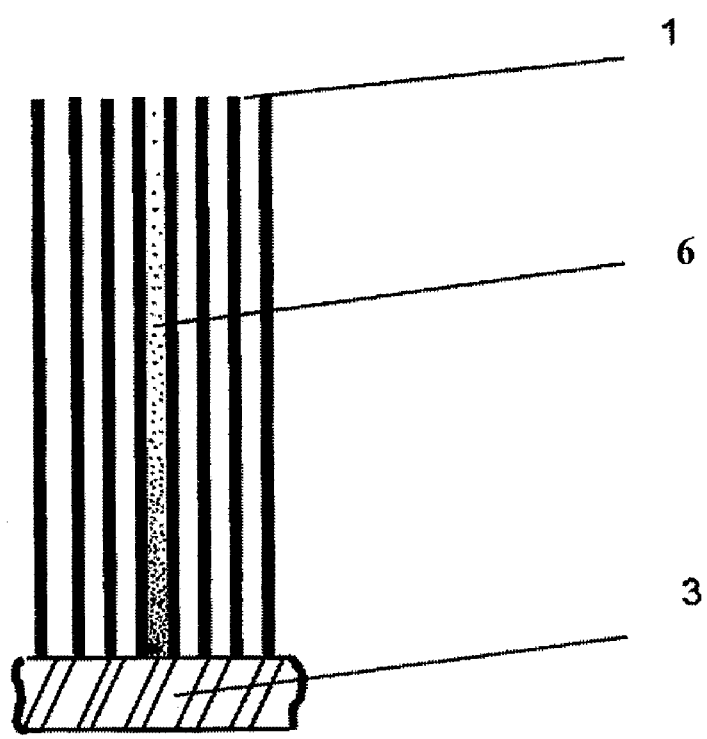

Procedure for Sampling and Treatment:

Reaction Enzyme(s)—Referring to FIGS. 1 and 2, artificial substrate(s) are to carried out in the micro-channels 1 of SDU 2 (which are not drawn to scale). SDU is a part of the device for sampling, trapping of cells (if present in sample) in micro-channels 1, and treatment procedures. Treatment procedures include: accurate addition of artificial substrate solution(s), antibody-enzyme complex and other reagents, if needed, to each channel and washing solutions for rinsing (for example surplus of antibody-enzyme complex or during changing artificial substrates when profile is investigated). All liquids pass through the device from the upper to lower side to prevent releasing trapped cells from the micro-channels.

Figure 3:
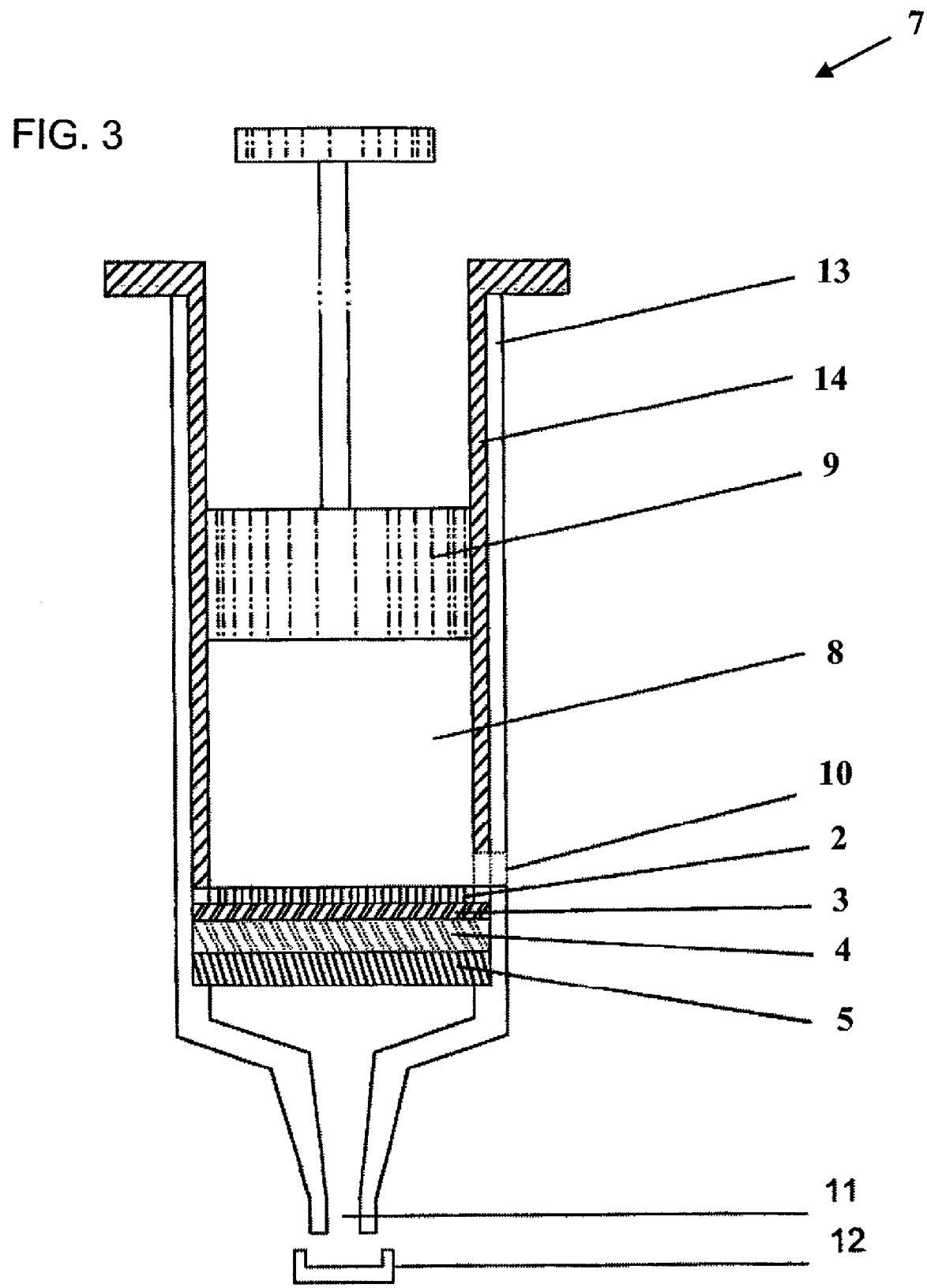
FIG. 3 is a cross-sectional view of a hand-held device for sampling and treatment of microorganism as well as enzyme or artificial substrate as applied to sampling-detecting unit.

Referring to FIG. 3 the general principle of a hand-held device 7 works as following:

1. A liquid sample, possibly containing microorganisms, is placed in the chamber 8 of the hand-held sampling device 7, as shown in FIG. 3.

2. A plunger, or forcer, 9 presses the sample through the SDU 2. Cells, if any, are trapped in the micro-channels 1 of SDU 2 on the surface of the filter 3.

3. A cap 12 closes the opening 11. Rotation of the inner cylinder 14 against the outer cylinder 13 opens a channel 10 to equalize air pressure (FIG. 3,6) and prevents reverse exit of trapped cells from the micro-channels 1. A channel for pressure equalization could have any another type of construction. For example closing and opening of channel 10 could be done by usage of the spigot.

4. A small amount(s) of artificial substrate(s) is added to the chamber of the device and the piston presses it into micro-channels of the SDU. All micro-channels are filled with artificial substrate(s).

5. The device is incubated for several minutes to around an hour at room temperature or higher. Incubation time depends on the object being analyzed.

6. The device is untwisted and the SDU is placed under a light or fluorescent microscope, scanning microscope or another eligible optical instrument.

7. The micro-channels containing live cells appear as colored (absorbent version) or fluorescent dots (FIG. 2). The diameter of the dots 15 μm (length of each micro-channel 500 μm and volume 88000 μm$^3$) in our experiments, but could be more or less. This size is big enough to use a small multiplication of the microscope: X.40-X100. Usage of a small multiplication allows a rapid scan of the entire SDU surface, in several minutes, to detect even single live cells and enumerate them. Automation of this process with micro-scanning systems could make this process faster.

In case of identification by EIA for a single cell, the following protocol steps need to be added after step 3:

3'. A solution of conjugated antibody with a marker enzyme is added to the chamber 8. The mixture is incubated for the time required to attach the conjugate to the antigens of entity.

3". The channel 10 is opened for equalization of pressure. The plunger 9 is pulled up, and the device chamber 8 is rinsed with a washing fluid that is pressed through with the plunger 9. This procedure could be done more than one time if needed.

In case of enzymatic profiles, steps 4, 5, 6 and 7 could be repeated a number of times. The levels of absorption or fluorescence in the micro-channels need to be measured by a micro-photometrical or micro-fluorimetrical instrument. This method allows identification of many different species in one sample, but it is more time-consuming and complicated than the EIA-method for identification of one sort of cells.

In case of bioaerosol sampling, adjust steps 1, 2 and 3 to the following:

Bioaerosol sampling could be done after removal of piston 9 from the device 7 and plug negative air pressure into nozzle, or tip 11.

Identification of single virus particles seems to be possible by the present invention (EIA version for single virus particle). Trapping of single virus particles in SDU could be realized by the usage of special filters such as membranes (ex. dialysis membrane), treating the inner walls of the micro-channels with specific antibodies, lectines or other reagents, or employment of magnetic particles.

Example 1

Detection of Live *Escherichia coli* Cells from Drinking Water

A 100 ml sample of water was pressed through a Device and SDU with a black non-fluorescent nitrocellulose filter. 2 ml of freshly made 4-Methylumbelliferyl-Beta-D-glucuronide (0.1 mg/ml) in distilled water was pressed through the SDU. All channels were filled by the solution of fluorogenic substrate. Incubation was for 20 minutes at 40 degrees Celsius. After incubation, the device was untwisted and the micro-channel plate with filter was placed under a fluorescent microscope: X60, λ excitation 340-380 nm, λ fluorescence 450 nm. Micro-channels containing live *E. coli* appeared as blue fluorescent dots. Micro-channels without cells or live cells of other species appear as black dots. The same results by other rapid methods could be reached in 6-8 hours.

Example 2

Identification of *Brucella melitensis* from Milk

A 100 ml sample of milk previously defatted was pressed through a Device and SDU with a white nitrocellulose filter. 50 ml of Phosphate buffer, pH 8.0, was pressed through the Device to wash out proteins and fat. 2 ml of standard conjugated antibody for *B. melitensis* surface antigens and Horseradish Peroxidase was added to the Device and slowly—part after part, during several minutes—pressed through the SDU. After that, 50 ml of distilled water was pressed through the SDU in order to wash out the rest of the conjugate. 2 ml of solution of 3,3',5,5'-Tetramethylbenzidine was added to the Device and pressed through the SDU. Incubation was for 40 minutes at 35° C. After incubation, the SDU with filter was placed under a light microscope; X60. Micro-channels containing *B. melitensis* appeared as blue dots. Other micro-channels appeared as white dots. Even one cell in 100 ml could be found in less than one hour. The regular procedure needs a preliminary growth period of at least 26-28 hours. Flow cytometry needs approximately the same amount of time as the method described here, but needs an instrument with a price of around $100,000 and highly qualified personnel. PCR reaches the same results in about two hours and involves a complicated technique.

What is claimed is:

1. A method for detecting one or more microorganisms contained in a liquid sample, said method capable of detecting a single microorganism in the liquid sample, comprising:

passing the liquid sample containing one or more microorganisms through a micro-channel plate in one direction from an upper surface of said micro-channel plate to a lower surface of said micro-channel plate, said micro-channel plate having formed therein a plurality of vertically elongated, parallel, micro-channels which are open at said upper surface and at said lower surface of said plate;

passing the liquid sample through a filter, said filter having an upper surface and a lower surface and said upper surface of said filter being positioned adjacent to the lower surface of said micro-channel plate;

trapping said one or more microorganisms inside one or more of said plurality of micro-channels on said upper surface of said filter;

adding an artificial substrate to said microchannels of said microchannel plate from said upper surface of said micro-channel plate to said lower surface of said micro-channel plate;

allowing said artificial substrate to react with an enzyme associated with said one or more microorganisms contained within one or more of said plurality of micro-channels;

incubating said artificial substrate and one or more microorganisms; and producing in one or more of said plurality of micro-channels a colored or fluorescent dot to identify said one or more microorganisms therein.

2. The method according to claim 1, wherein said enzyme associated with said one or more microorganisms is produced by one of said one or more microorganisms.

3. The method according to claim 1, wherein said enzyme associated with said one or more microorganisms is an antibody-enzyme conjugate that is attached to one of said one or more microorganisms.

4. The method according to claim 1, wherein said artificial substrate is selected from the group consisting of 2-Nitrophenol, 4-Nitrophenol, 5-4-chloro-3-indoxol, 3-Indoxol, 5-Bromo-6-chloro-3-indoxol, 6-Chloro-3-indoxol, 5-Iodo-3-indoxol, N-Methylindoxol, 3,3',5,5'-Tetramethylbenzidine dihydroxhloride, 4-Methylumbelliforone, 7-Amido-4-methylcoumarin, Fluorescein, and Eosine.

5. The method according to claim 1, wherein said colored or fluorescent dot is detected by fluorometry.

6. The method according to claim 1, wherein said colored or fluorescent dot is detected by colorimetry.

7. The method of claim 1, further comprising detecting, identifying and/or enumerating said one or more microorganisms in said one or more micro-channels using an optical instrument.

8. The method of claim 7, wherein the optical instrument is selected from the group consisting of a light microscope, a fluorescent microscope and other optical instruments.

9. The method of claim 1 wherein the step of passing the liquid sample through the filter is performed by pressing the sample with pressure.

10. The method of claim 1 wherein the steps of allowing said artificial substrate to react with an enzyme associated with said one or more microorganisms, incubating, and producing a colored or fluorescent dot are repeated a plurality of times on the micro-channel plate to obtain enzymatic profiles for the identification of a plurality of species from one sample.

11. The method of claim 1 wherein said detecting one or more microorganisms is performed on a single cell without requiring preliminary growth.

* * * * *